(12) United States Patent
Razzano et al.

(10) Patent No.: US 8,908,162 B2
(45) Date of Patent: Dec. 9, 2014

(54) SYSTEM FOR ALIGNING A COLLIMATOR AND AN ALIGNMENT RING

(75) Inventors: Michael R. Razzano, Marietta, GA (US); Raynold Lee Saar, Marietta, GA (US)

(73) Assignee: IDI Dental, Inc., Marietta, GA (US)

( * ) Notice: Subject to any disclaimer, the term of this patent is extended or adjusted under 35 U.S.C. 154(b) by 355 days.

(21) Appl. No.: 13/404,413

(22) Filed: Feb. 24, 2012

(65) Prior Publication Data

US 2012/0218544 A1  Aug. 30, 2012

Related U.S. Application Data

(60) Provisional application No. 61/446,328, filed on Feb. 24, 2011.

(51) Int. Cl.
| | |
|---|---|
| G01N 21/00 | (2006.01) |
| G01B 11/00 | (2006.01) |
| A61B 6/06 | (2006.01) |
| G01B 7/02 | (2006.01) |
| G01B 11/27 | (2006.01) |
| A61B 6/08 | (2006.01) |
| A61B 6/00 | (2006.01) |
| A61B 6/14 | (2006.01) |

(52) U.S. Cl.
CPC ............... *G01B 11/272* (2013.01); *A61B 6/145* (2013.01); *A61B 6/06* (2013.01); *G01B 7/023* (2013.01); *A61B 6/08* (2013.01); *A61B 6/586* (2013.01); *A61B 6/14* (2013.01)
USPC ............................................. 356/72; 356/400

(58) Field of Classification Search
CPC .......... A61B 6/58; A61B 6/587; A61B 6/581; A61B 6/582; A61B 6/583; A61B 6/584; A61B 6/585; A61B 7/023; A61B 6/06; A61B 6/08; A61B 6/14; A61B 6/145
USPC ................... 356/400, 72, 614–624, 213–236; 250/221, 223 R, 227.11, 462.1; 378/20, 378/34, 38, 65, 68, 98, 98.8, 102, 117, 147, 378/153, 168, 169, 191, 193, 197, 378/205–207; 128/920
See application file for complete search history.

(56) References Cited

U.S. PATENT DOCUMENTS

| | | |
|---|---|---|
| 3,628,021 A | 12/1971 | MacDonald |
| 4,158,776 A | 6/1979 | Barrett |
| 4,167,675 A | 9/1979 | Studberg et al. |
| 4,278,888 A | 7/1981 | Wagner |
| 4,426,726 A | 1/1984 | Cheetham |

(Continued)

FOREIGN PATENT DOCUMENTS

| | | | |
|---|---|---|---|
| EP | 2287069 A1 | * | 2/2011 |
| JP | 2005063696 A | * | 3/2005 |

*Primary Examiner* — Kara E Geisel
*Assistant Examiner* — Violeta A Prieto
(74) *Attorney, Agent, or Firm* — Woodard, Emhardt, Moriarty, McNett & Henry LLP

(57) ABSTRACT

Disclosed is a system for aligning a collimator tube with an alignment ring used to hold a film or sensor aligned with the collimator tube. The disclosed alignment system includes a light source, a light detector, and a reflective surface, where, when the collimator and alignment ring are aligned, light emitted from the light source reflects off the reflective surface and is received by the light detector.

15 Claims, 17 Drawing Sheets

(56) References Cited

U.S. PATENT DOCUMENTS

| | | | |
|---|---|---|---|
| 4,896,343 A * | 1/1990 | Saunders | 378/95 |
| 5,235,337 A * | 8/1993 | Clark et al. | 342/51 |
| 5,537,453 A | 7/1996 | Williams et al. | |
| 5,631,943 A | 5/1997 | Miles | |
| 5,745,545 A | 4/1998 | Hughes | |
| 5,781,610 A | 7/1998 | Miles | |
| 6,038,287 A | 3/2000 | Miles | |
| 6,267,503 B1 | 7/2001 | McBride | |
| 6,356,616 B1 | 3/2002 | Oshino | |
| 6,597,006 B1 * | 7/2003 | McCord et al. | 250/559.19 |
| 6,694,169 B2 | 2/2004 | Kennedy, II et al. | |
| 6,735,360 B2 * | 5/2004 | Mao et al. | 385/33 |
| 6,736,776 B2 | 5/2004 | Miles | |
| 6,821,017 B1 * | 11/2004 | Tankersley | 378/207 |
| 6,998,629 B2 * | 2/2006 | Fan | 250/559.29 |
| 7,077,568 B2 | 7/2006 | Hornegger | |
| 7,194,064 B2 | 3/2007 | Razzano et al. | |
| 7,382,860 B2 | 6/2008 | Razzano et al. | |
| 7,736,055 B2 * | 6/2010 | Hornig | 378/206 |
| 2005/0058256 A1 * | 3/2005 | Beimler et al. | 378/162 |
| 2005/0190890 A1 | 9/2005 | Schmitt | |
| 2006/0069591 A1 | 3/2006 | Razzano | |
| 2006/0188070 A1 | 8/2006 | Razzano et al. | |
| 2006/0274890 A1 | 12/2006 | Razzano | |
| 2006/0285636 A1 | 12/2006 | Razzano | |
| 2007/0003019 A1 | 1/2007 | Qian | |
| 2007/0025525 A1 * | 2/2007 | Gilath | 378/206 |
| 2008/0165933 A1 * | 7/2008 | Hornig | 378/206 |
| 2008/0298543 A1 | 12/2008 | Razzano | |
| 2009/0257564 A1 * | 10/2009 | Kito et al. | 378/206 |
| 2009/0296881 A1 * | 12/2009 | Hornig | 378/37 |
| 2011/0194101 A1 * | 8/2011 | Tachizaki et al. | 356/72 |
| 2011/0198507 A1 * | 8/2011 | Takegami | 250/370.08 |

* cited by examiner

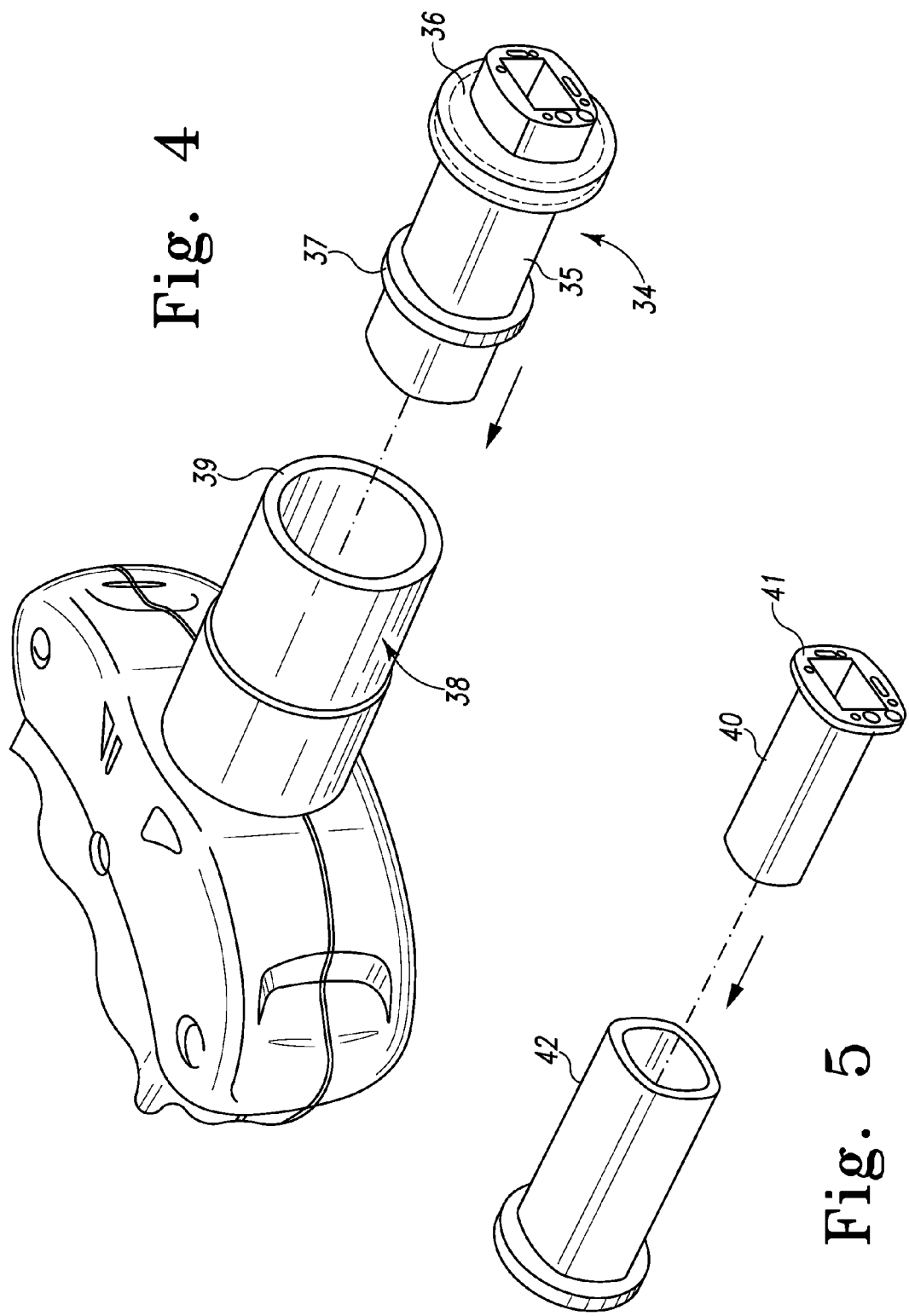

SYSTEM FOR ALIGNING A COLLIMATOR AND AN ALIGNMENT RING

This application claims the benefit of U.S. Provisional Application No. 61/446,328, filed Feb. 24, 2011, which is hereby incorporated by reference

BACKGROUND

In today's medical profession, there are various ways to capture images of patients, such as images captured for diagnostic purposes. For example, a medical professional such as a dentist can use a traditional x-ray device to capture a film-based x-ray image of the patient's mouth. Medical professionals can also capture an x-ray image in a digital fashion using a digital x-ray device that has a computer workstation and a sensor. Digital cameras are also used by medical professionals to capture still and video images for later storage on a computer in the patient record. Each of the devices and systems typically require separate systems and pieces of equipment. There is a need for improved devices, systems and methods for capturing images.

BRIEF DESCRIPTION OF THE DRAWINGS

FIG. 4 is a partial perspective view of a collimator tube of one shape being converted to a collimator tube of another shape using a collimator tube adapter.

FIG. 5 is a perspective view of a collimator tube and an insert.

DETAILED DESCRIPTION

Figure 1:
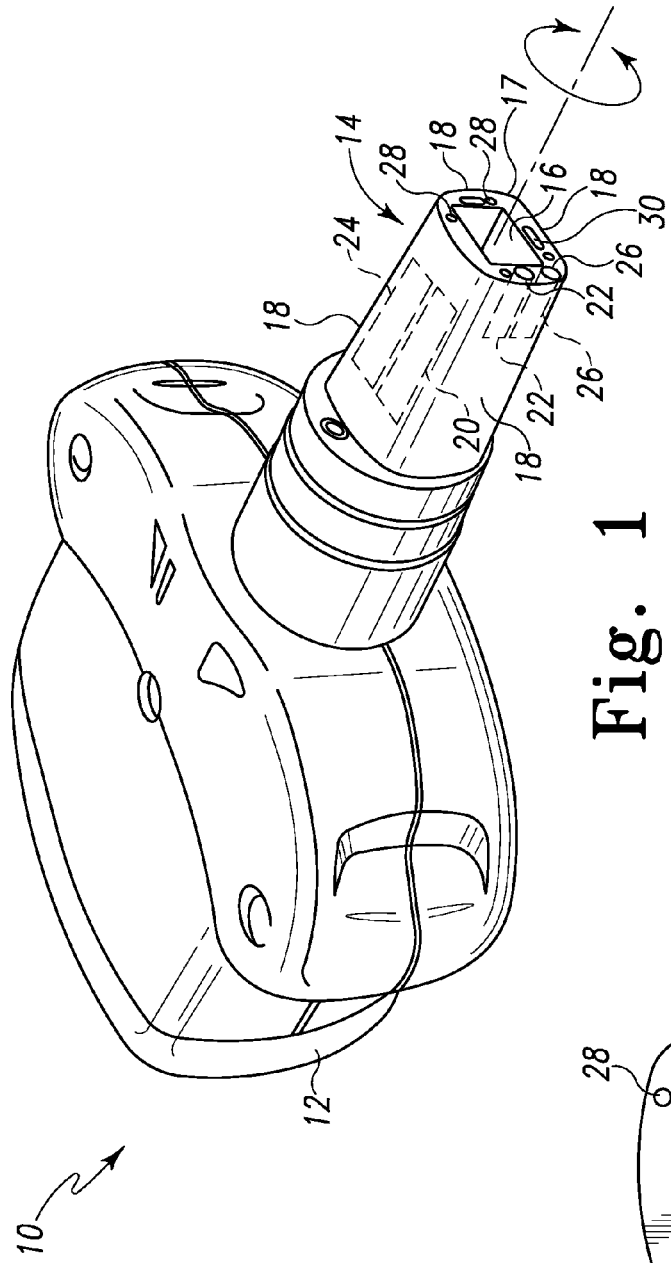
FIG. 1 is a perspective view of an image capture device with an x-ray collimator tube.

Reference will now be made to certain embodiments and specific language will be used to describe the same. It will nevertheless be understood that no limitation of the scope of this disclosure and the claims are thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

The present disclosure relates to an image capture device, system and method for use in capturing medical images. A collimator tube includes one or more integrated devices, such as a radio frequency transmitter, a camera, a frame grabber, or a transilluminator light. In one embodiment, the integrated devices are integrated within one or more walls of the collimator tube. The integrated devices are used instead of or in addition to an x-ray generator, which is coupled to the collimator tube. The camera is used to capture digital images. The camera is either a camera port for plugging in an external camera, such as an intra-oral camera, or is wholly contained within the collimator tube. The radio frequency transmitter transmits digital data to a computer. The frame grabber captures digital data for display on a display device. The transilluminator light can illuminate an area for visual inspection and/or digital capture. A receptor holder includes a docking port for docking a sensor that is used for digital x-ray image capture.

Referring to FIG. 1, one embodiment of the image capture device is illustrated and indicated generally at 10. Image capture device 10 is operable to capture x-ray images. The image capture device 10 illustrated in FIG. 1 includes x-ray generator 12 and collimator tube 14. Collimator tube 14 serves as the means for focusing x-rays produced by the x-ray generator 12. Alternatively or additionally, collimator tube 14 also decreases scatter radiation and/or decreases absorbed radiation, thereby lowering the patient's x-ray dose. In one embodiment, collimator tube 14 has a square shape in cross section. Collimator tube 14 can also be rectangular, star, cross or round in cross section shape, as a few additional non-limiting examples.

In one embodiment, collimator tube 14 is fixed to x-ray generator 12 and cannot be removed. In another embodiment, collimator tube 14 is detachable from x-ray generator 12, such as by removing one or more screws or other securing means. Alternatively or additionally, collimator tube 14 can be a collimator tube of one shape that replaces a previously attached collimator tube of a different shape. One non-limiting example includes detaching a round-shaped collimator tube and replacing it with a rectangular-shaped collimator tube.

Collimator tube 14 has a tunnel 16 for emitting x-rays and a receptacle 30 for receiving a sliding bar of a receptor holder. Collimator tube 14 has an end 17 that serves one or more purposes. One purpose of end 17 is for coupling a receptor holder to collimator tube 14. Collimator tube 14 has one or more devices integrated within walls 18. In one embodiment, at least one integrated device is visible at least in part from end 17. In one embodiment, collimator tube 14 has a radio frequency transmitter 20, a camera/port 22, a frame grabber 24, and/or a transilluminator light 26 integrated within one or more walls 18.

Each of these integrated devices will now be described in further detail with reference to FIGS. 1 and 2. Radio frequency (RF) transmitter 20 is operative to send data captured with image capture device 10 to an RF receiver external to image capture device 10. For example, the RF receiver may be coupled to a remotely-located computer for the display and/or processing of images captured by the device 10. As one non-limiting example, RF transmitter 20 can transmit data captured with camera 22 to an external computer. In this way, images captured by image capture device 10 may be downloaded to a computer system for current and/or later use without the need to physically couple the image capture device 10 to the computer. This greatly improves the maneuverability and usefulness of the image capture device 10.

Figure 3:
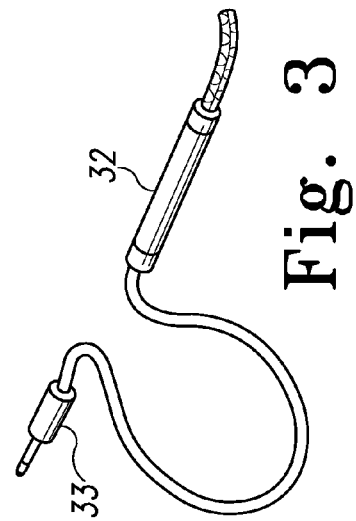
FIG. 3 is perspective view of an intra-oral camera that can be connected to the collimator tube.

In one embodiment, the camera 22 is built into the collimator tube 14 and is able to capture images visible from a lens or aperture formed into the end of the collimator tube 14. In another embodiment, camera 22 is an electrical port for allowing an external camera device to plug into collimator tube 14 for transmission of data from the external camera device to the collimator tube 14 integrated devices. One non-limiting example of an external camera device includes intra-oral camera 32 as shown in FIG. 3. The intra-oral camera 32 includes an electrical plug 33 that interfaces with the camera 22 port in the collimator tube 14 for transmitting data captured by the camera 32. Cameras 22 and 32 are operative to capture still images and/or video images in various embodiments. Provision of the external intra-oral camera 32 allows for easy access to the inner regions of the patient's mouth.

In one embodiment, frame grabber 24 is operative to capture still and/or video images for display on an external video display device, such as on a television or a computer display, as is known in the art. Frame grabber 24 is integrally formed with collimator tube 14 to receive image information from one of the image devices integrated with image capture device 10, such as cameras 22 and 32 or the x-ray image receptor 54 (see FIG. 8). The output of frame grabber 24 is preferably coupled to the RF transmitter 20 for transmission of the frame data to a receiving computer and/or display device.

Transilluminator light 26 aids the image capture process by allowing for a light to be shined through a tooth, body or organ, as a few non-limiting examples. The light that is transmitted through the tooth can then be captured using the cameras 22 and 32. For use with camera 22 formed integrally with the collimator tube 14, means must be provided for directing the light from the transilluminator light 26 to the opposite side of the tooth as camera 22. This may be done by use of an appropriate mirror (not shown), or by making the transilluminator light 26 an external device that plugs into a port in the collimator tube 14, similar to the intra-oral camera 32. Additionally, the transilluminator light 26 may emit light from the collimator tube 14 and the light transmitted through the tooth may be captured using intra-oral camera 32.

Various other device combinations are also possible, such as fewer or additional devices than described herein, or a combination of those described. Power may be supplied to these devices by using the internal power supply of the image capture device 10, as will be apparent to those skilled in the art after reference to the above description.

In one form, collimator tube 14 has contact sensor receptacles 28 that are used to mate an image receptor holder (see FIGS. 8-10) to the collimator tube 14. Contact sensor receptacle 28 can be one or more of various types, such as electrical, mechanical, optical, fiber optic, magnetic or of other connection types as would occur to one in the art. As one non-limiting example, contact sensor receptacles can be used to form a purely mechanical connection between the image receptor holder and the collimator tube 14. Alternatively or additionally, contact sensor receptacles 28 can be used to ensure a receptor holder is attached before firing x-ray generator 12. Alternatively or additionally, one or more lights can be illuminated to indicate the status of the connection, such as green to indicate a proper connection with collimator tube 14 has been made and the x-ray generator is ready to fire, and red to indicate the x-ray generator is not ready to fire, to name a few examples. Alternatively or additionally, a light can be illuminated to indicate that a proper connection has been made, and the light is not illuminated when a proper connection is not made. Alternatively or additionally, an audible sound can be emitted to indicate that a proper connection has been made. In one embodiment, contact sensor receptacles 28 are used with receptor holder 50 illustrated in FIGS. 8-10. Alternatively or additionally, collimator tube 14 has a contact end receptacle 30 formed therein and operative to receive a contact end of a receptor holder. In one embodiment, contact end receptacle 30 is used with the receptor holder illustrated in FIG. 11.

In yet another embodiment, as illustrated in FIG. 4, collimator tube adapter 34 is used to convert collimator tube 38 to a different shape. As one non-limiting example, collimator tube adapter 34 is used to convert collimator tube 38 from a round shape to a rectangular or other shape. Collimator tube adapter 34 includes cone 35, cap 36, and spacer 37. Cap 36 can slide to adjust cone 35 to different depths so cone 35 can fit properly inside collimator tube 38. Various mechanisms can be used to lock cap 36 into a desired location on cone 35, such as using detents or a snap ring, to name a few non-limiting examples. Spacer 37 is used to help secure cone 35 inside collimator tube 38, since cone 35 is a different shape than collimator tube 38. Various types of spacers can be used, such as a washer or an o-ring, to name a few non-limiting examples. Cap 36 is operable to form a seal around end 39 of collimator tube 38.

Although not numbered on FIG. 4 to preserve clarity, in one embodiment, collimator tube adapter 34 has one or more devices integrated within its walls. These devices can be integrated within walls of collimator tube adapter 34 instead of or in addition to devices integrated in collimator tube 38. Collimator tube adapter 34 and collimator tube 38, when used together, can include the same devices and perform the same functions as described herein with respect to collimator tube 14 of image capture device 10 on FIG. 1.

As shown in FIG. 5, insert 40 is a step-down insert that can be inserted into collimator tube 42 to make the image capture area smaller. Alternatively or additionally, insert 40 can be used to add integrated devices to existing collimator tube 42. One non-limiting example of a situation in which insert 40 can be used is to capture an image more precisely on a smaller image receptor than collimator tube 42 would capture alone. Alternatively or additionally, insert 40 can be inserted into collimator tube adapter 34 of FIG. 4 to make the image capture area even smaller. Although not numbered on FIG. 5 to preserve clarity, instead of or in addition to the integrated devices included within the walls of collimator tube 14 or collimator tube adapter 34, insert 40 can optionally include one or more devices integrated within its walls. Insert 40 can optionally have at least one integrated device visible at least in part from end 41. Details about these integrated devices and how they function are described in detail in reference to FIGS. 1 and 4. Alternatively or additionally, insert 40 can be used to add one or more integrated devices to existing collimator tube 42 without reducing the size of the image capture area any more than necessary to house the integrated devices.

Figure 6:
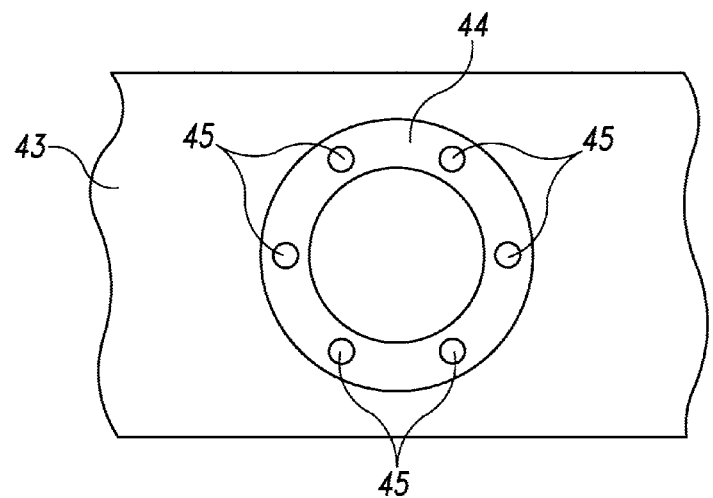
FIG. 6 is a front end view of an x-ray device without a collimator tube attached.
Figure 7:
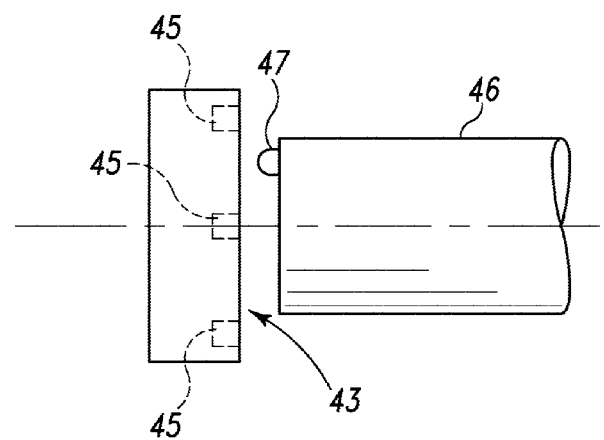
FIG. 7 is a partial elevational view of a collimator tube mating with the x-ray device of FIG. 6 in a manner that allows rotation of the collimator tube.

As shown in FIGS. 6-7, in one embodiment, a collimator tube and/or x-ray generator can rotate with respect to the other. Front end of x-ray generator 43 can optionally include a circular or other path 44 with indentations 45. Collimator tube 46 mates with front end of x-ray generator 43 with one or more detents 47 that lock and unlock into one or more of indentations 45 when rotated along path 44. Circular or other path 44 can be a track or other types as would occur to one of ordinary skill in the art so as to allow collimator tube 46 inserted therein to remain physically attached to the front end of x-ray generator 43 and then click into position when coming into contact with one or more detents 47. In an alternative embodiment, the indentations and path are present on collimator tube 46 and one or more detents are present on the front end of x-ray generator 43.

Figure 2:
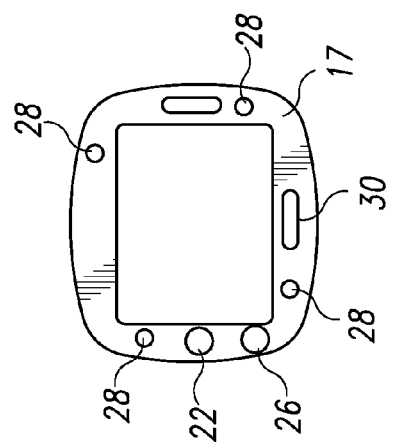
FIG. 2 is a front end view of a collimator.
Figure 9:
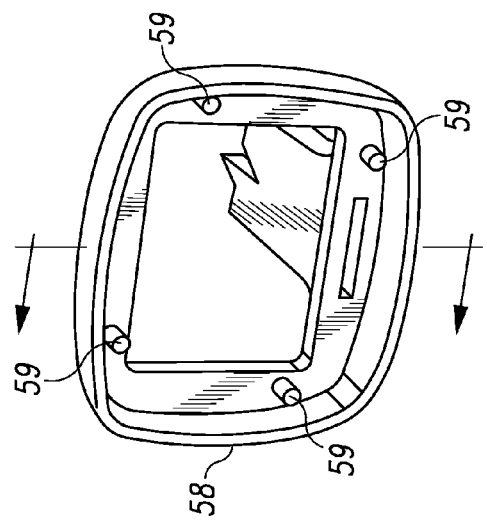
FIG. 9 is a back end view of a connection end of the receptor holder of FIG. 10.
Figure 10:
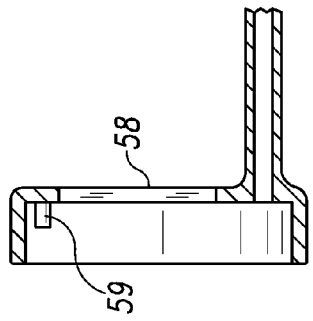
FIG. 10 is a partial cross-section view of the connection end of the receptor holder of FIG. 10.
Figure 8:
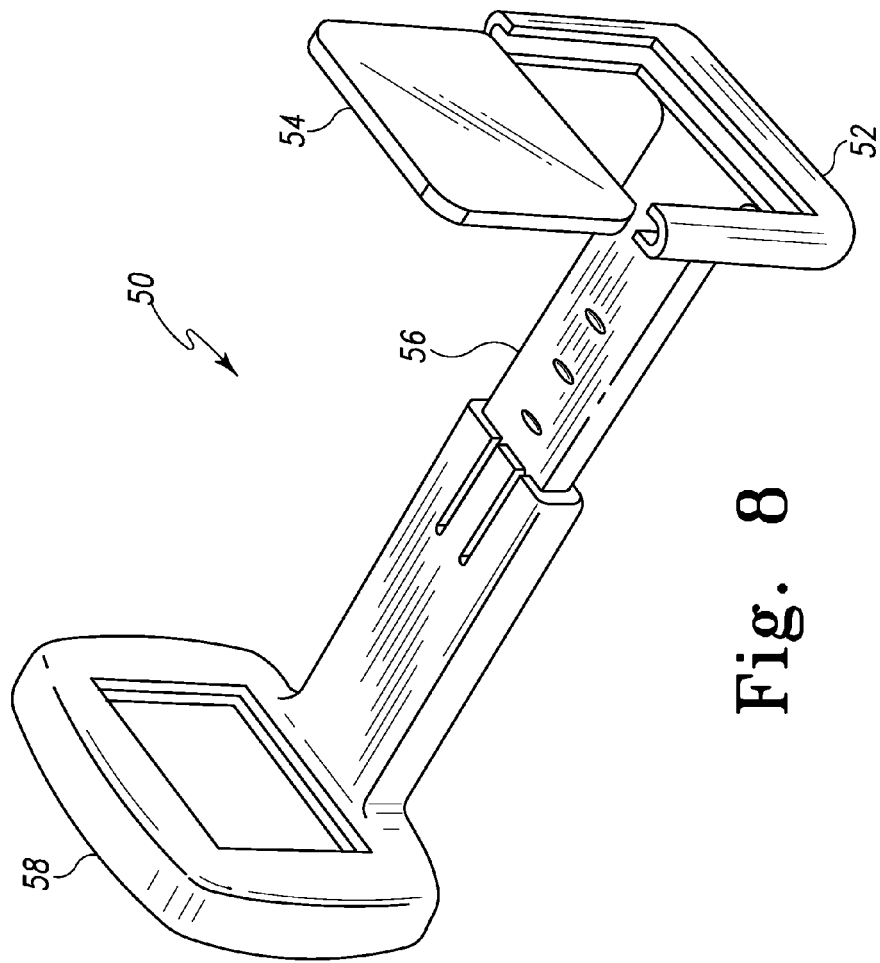
FIG. 8 is a side perspective view of a first embodiment receptor holder.

Referring now to FIGS. 8-10 with continued reference to FIGS. 1-2, a first embodiment receptor holder 50 is illustrated. Receptor holder 50 has a holder end 52 that is operative to hold an image receptor 54, such as x-ray film or a digital charge-coupled device (CCD) sensor, as a few non-limiting examples. Receptor holder 50 has an adjustable bar 56 for adjusting the distance of holder end 52 from a connection end 58. In one embodiment, connection end 58 has a square shape. Connection end 58 can also be rectangular, star, cross or round in cross section shape, as a few additional non-limiting examples.

As shown in FIGS. 9 and 10, connection end 58 may have contact sensors 59 that are operative to be connected with collimator tube 14 through contact end receptors 28 formed in collimator tube end 17. In one embodiment, contact sensors 59 are used to ensure that the receptor holder 50 is attached to collimator tube 14 before firing the x-ray generator 12. In this embodiment, contact end receptors 28 are formed with sensors that determine when contact sensors 59 are inserted therein. As one example, each receptor 28 may have two metallic elements that are short circuited by a conductive contact sensor 59 when the connection end 58 is fitted to the collimator tube end 17. Coupling these metallic elements to the firing circuitry of the image capture device 10 can prevent the image capture device 10 from being fired unless the receptor holder 50 is properly fitted, as will be apparent to those skilled in the art from the above description. In one embodiment, receptor holder 50 is used to capture film-based x-ray images. In another embodiment, receptor holder is used to capture digitized x-ray images. Alternatively or additionally, receptor holder 50 can be used to hold a mirror for reflecting an image to be captured with camera 22, or for reflecting transilluminator light 26 for capture with camera 22.

Figure 11:
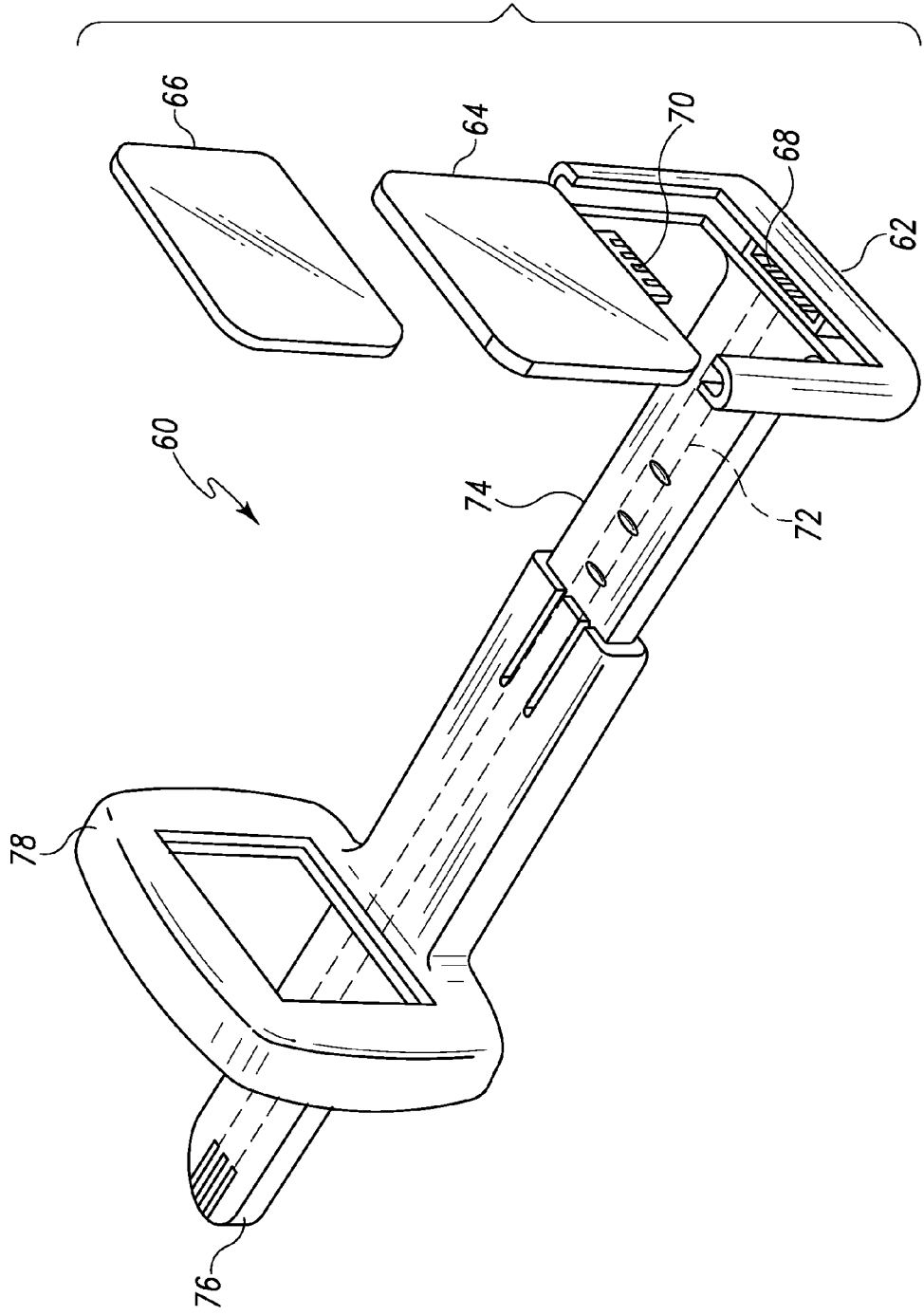
FIG. 11 is a side perspective view of a second embodiment receptor holder.

Referring now to FIG. 11 with continued reference to FIGS. 1-2, a second embodiment receptor holder 60 is illustrated. Receptor holder 60 has a holder end 62 that is operative to hold a digital sensor 64 or x-ray film 66. Alternatively or additionally, receptor holder 60 can be used to hold a mirror for use with camera 22 or transilluminator light 26, as described hereinabove. Holder end 62 contains a docking port 68 to enable connection of digital sensor 64, which includes a sensor end 70 for electrical mating to docking port 68 of holder end 62. In one embodiment, wiring 72 is connected to docking port 68 at holder end 62. Wiring 72 runs through adjustable bar 74 and connects to contact end 76. Receptor holder 60 has adjustable bar 74 for adjusting the distance of holder end 62 from contact end 76. Contact end 76 can be inserted into contact end receptacle 30 of collimator tube 14 to couple receptor holder 60 to collimator tube 14.

Upon insertion of contact end 76 into contact end receptacle 30, connection frame 78 fits over end 17 of collimator tube 14. In one embodiment, when digital sensor 64 is docked in docking port 68 and x-ray generator 12 is fired, digital data is captured using sensor 64 and travels through wiring 72 to contact end 76 and to frame grabber 24 of collimator tube 14. In another embodiment, digital data captured using sensor 64 travels through wiring 72 to contact end 76 and to radio frequency transmitter 20 of collimator tube 14. In this embodiment, a frame grabber may be present in the remote computer.

In an alternate embodiment, receptor holder 50 (FIG. 8) and/or receptor holder 60 (FIG. 11) has an integrated radio frequency transmitter, such as within the walls of the holder.

Figure 12:
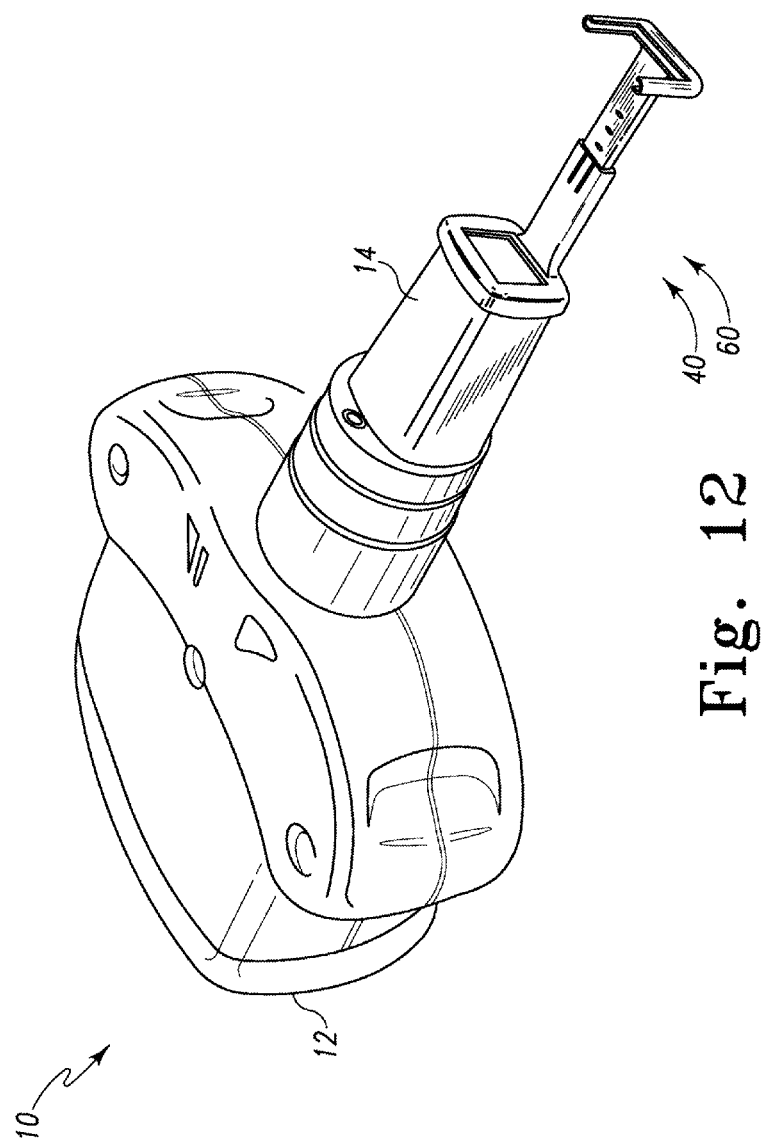
FIG. 12 is a perspective view of an image capture device illustrating an x-ray generator, collimator tube, and receptor holder.

FIG. 12 illustrates an embodiment of the system, comprising image capture device 10 with x-ray generator 12, collimator tube 14, and receptor holder (40 or 60) attached.

Figure 13:
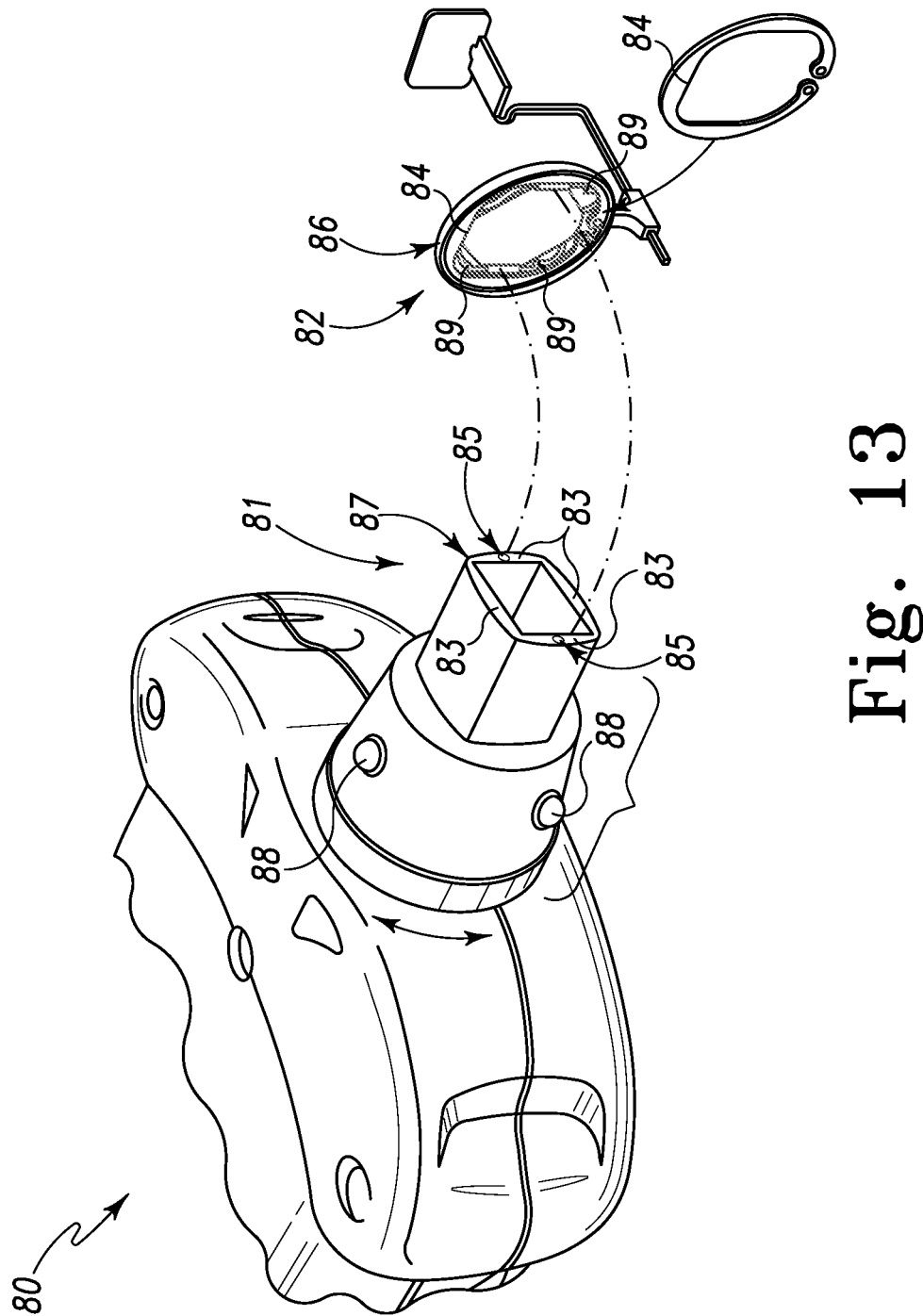
FIG. 13 is a side perspective view of an image capture device illustrating an x-ray generator, collimator tube, and receptor holder.

FIG. 13 illustrates an image capture device having an x-ray generator 80, collimator tube 81, and receptor holder 82. Film alignment ring 86 of receptor holder 82 fits around outer perimeter 87 of collimator tube 81. In one embodiment, notches 89 in receptor holder 82 are tapered and/or indented to help film alignment ring 86 align properly with collimator tube 81. Receptor holder 82 can be coupled to collimator tube 81 by magnetism when magnets 83 of collimator tube 81 come into contact with conductor/magnet interface metal snap ring 84 of receptor holder 82. Alternatively or additionally, snap ring 84 completes the circuit between low voltage electrical contact 85 and magnets 83, causing LED lights 88 to illuminate to indicate that receptor holder 82 is properly coupled to collimator tube 81. Magnets 83 and/or electrical contacts 85 can be located at one or more of various locations on outer perimeter 87 or other locations as would occur to one of ordinary skill in the art. In one embodiment, collimator tube 81 is a replacement for a prior collimator tube of a differing shape, such as a rectangular tube replacing a round tube, to name a non-limiting example. Alternatively or additionally, magnets 83, electrical contacts 85, and LED lights 88 can be included in an adaptor that is attached to an existing collimator tube. In one embodiment, receptor holder 82 and collimator tube 81 maintain a magnetic connection sufficient to couple them together but also allow them to easily separate from each other upon contact, such as with a doctor or patient touching receptor holder 82. Alternatively or additionally, the positioning bar of receptor holder 82 has notches that allow the user to identify the distance at which the film was positioned, such as to allow for re-taking another image in the future at the same distance.

Although not shown on FIG. 13 to preserve clarity, in one embodiment, collimator tube 81 has one or more devices integrated within its walls. Collimator tube 81 can include the same devices and perform the same functions as described herein with respect to collimator tube 14 of image capture device 10 on FIG. 1.

Figure 14:
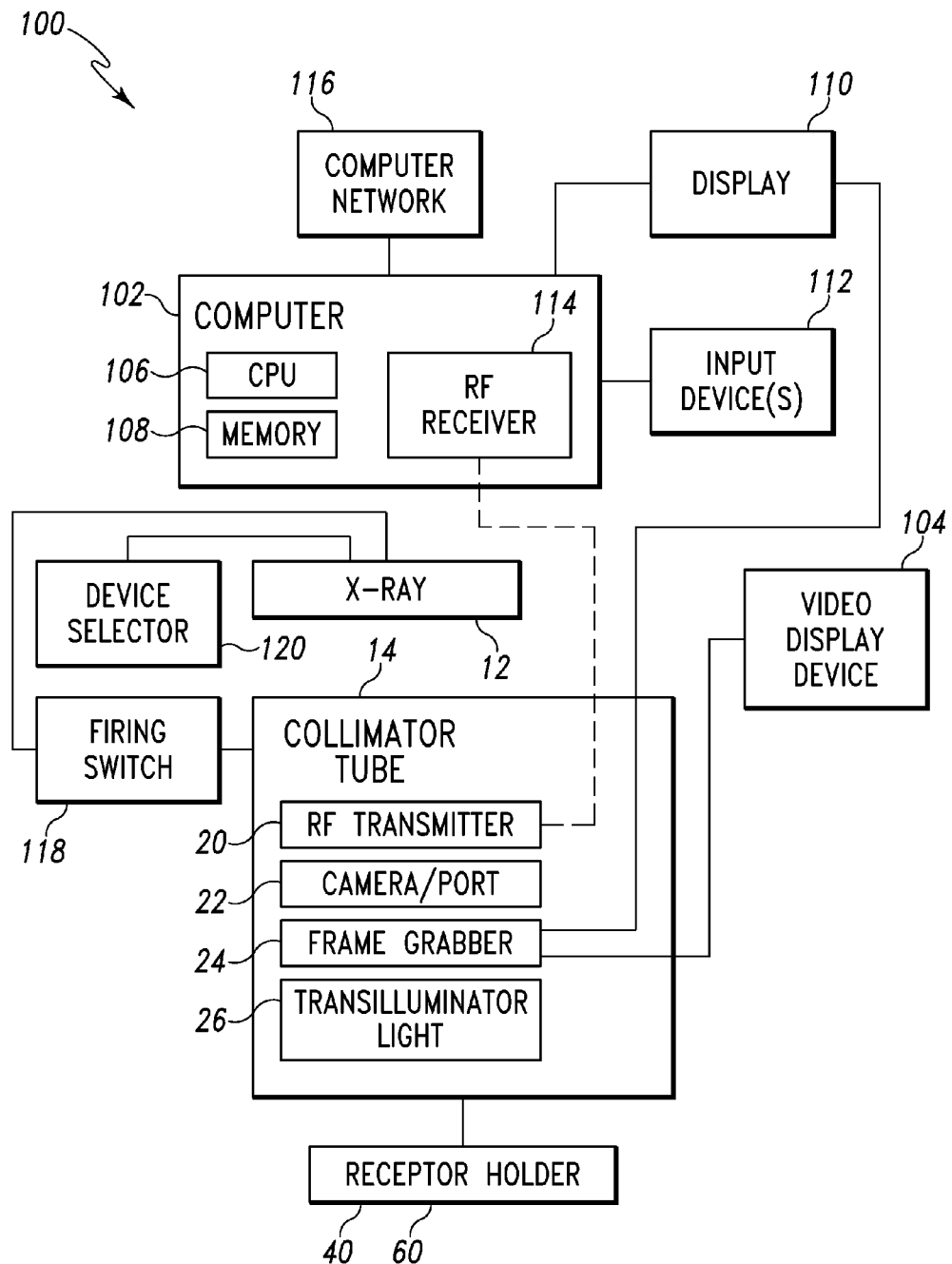
FIG. 14 is a diagrammatic view of a system for use with the image capture device of FIGS. 1-13.
Figure 15:
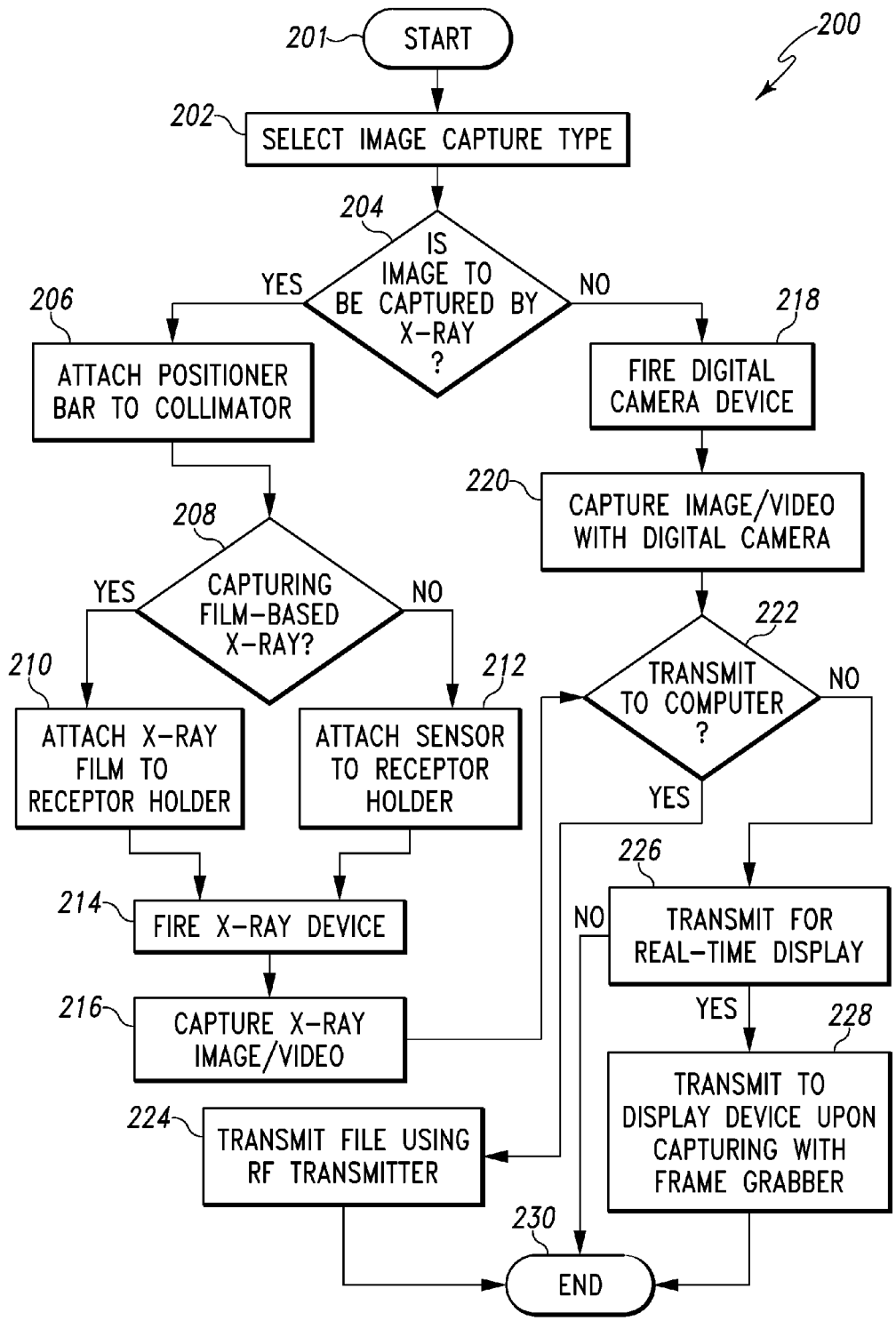
FIG. 15 illustrates a high-level process flow diagram for the system of FIG. 1 and the image capture device of FIGS. 1-13.

Reference will now be made to FIGS. 14 and 15 with continued reference to FIGS. 1-13 to illustrate a system and method for using image capture device 10. The same reference numerals are used to refer to elements that have already been introduced. FIG. 14 is a diagrammatic view of system 100. System 100 includes computer 102, x-ray generator 12, collimator tube 14, receptor holder (40 or 60), and video display device 104. It should be understood computer 102 may be arranged to include both a client and server, just a client, or just a server. Furthermore, it should be understood that while one computer is illustrated, more than one computer may be utilized in alternative embodiments.

Computer 102 includes one or more processors or CPUs 106 and one or more types of memory 108. Each memory 108 may include a removable memory device, although not shown to preserve clarity. The processor 106 may be comprised of one or more components configured as a single unit. Alternatively, when of a multi-component form, a processor 106 may have one or more components located remotely relative to the others. One or more components of each processor 106 may be of the electronic variety defining digital circuitry, analog circuitry, or both. In one embodiment, processor 106 is of a conventional, integrated circuit microprocessor arrangement, such as one or more PENTIUM III or PENTIUM 4 processors supplied by INTEL Corporation of 2200 Mission College Boulevard, Santa Clara, Calif. 95052, USA.

Memory 108 (removable or generic) is one form of a computer-readable device. Memory 108 may include one or more types of solid-state electronic memory, magnetic memory, or optical memory, just to name a few. By way of non-limiting example, memory 108 may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, memory 108 may be volatile, nonvolatile, or a hybrid combination of volatile and nonvolatile varieties.

Computer 102 includes a display 110 and one or more input devices 112. Input devices 112 may include one or more operator input devices such as a keyboard, electronic pen input device, mouse, track ball, light pen, to name just a few representative examples. Computer 102 includes a radio frequency (RF) receiver 114 for receiving data transmitted by radio frequency transmitters. Alternatively or additionally, computer 102 includes a printer. In one embodiment, computer 102 is disconnected from computer network 116. In another embodiment, computer 102 is connected to network 116.

Although only one computer 102 is shown to preserve clarity, more computers could also be present. In such instances, multiple computers 102, displays 110, and input devices 112 may be of the same respective type, or a heterogeneous combination of different computing devices. When more computers are present, computer 102 can be coupled to other computers over computer network 116. Computer network 116 could be in the form of a Local Area Network (LAN), Municipal Area Network (MAN), Wide Area Network (WAN), such as the Internet, a combination of these, or such other network arrangement as would occur to those skilled in the art. The one or more features provided by computer 102 can be provided on the same computer or varying other arrangements of computers at one or more physical locations.

X-ray generator 12 is operable to generate x-ray images. Collimator tube 14 serves as the means for focusing x-rays for x-ray device 12, and also includes additional integrated devices. Alternatively or additionally, collimator tube 14 also decreases scatter radiation and/or decreases absorbed radiation, thereby lowering the patient's x-ray dose. In one embodiment, collimator tube 14 has a radio frequency (RF) transmitter 20 that can communicate with RF receiver 114 of computer 102. Alternatively or additionally, collimator tube 14 has an integrated camera 22. In one embodiment, camera 22 is a camera port for allowing an external camera device to plug into collimator tube 14. One non-limiting example of an external camera device includes an intra-oral camera 32 of FIG. 3. In another embodiment, camera 22 is wholly contained within collimator tube 14.

Alternatively or additionally, collimator tube 14 includes frame grabber 24 for capturing of and transmission of still and/or video images to video display device 104 and/or to display 110 of computer 102. Frame grabber 24 may also transfer data to RF transmitter 20. In one embodiment, collimator tube 14 includes transilluminator light 26. Transilluminator light 26 allows for shining a light through a tooth, body or organ, to name a few non-limiting examples.

X-ray generator 12 and collimator tube 14 are coupled to firing switch 118 and device selector 120. In one embodiment, a single firing switch 118 is used to fire whatever device is selected by device selector 120. In another embodiment, each image capture device has its own firing switch 118, and thus device selector 120 is not used. In some embodiments, firing switch 118 comprises a pair of switches which must both be pressed to activate the chosen device.

The operating logic of system 100 can be embodied in signals in programming instructions, dedicated hardware, transmitted over computer network 116, or a combination of these.

As one non-limiting example, system 100 can be used by a dentist to capture patient images. The image capture apparatus, system and method of the current disclosure are not limited to use in dentistry, or the field of medicine, as will be understood by one in the art. The current disclosure can be used in various industries where capturing an x-ray image or digital image would be useful. Referring additionally to FIG. 15, one embodiment for implementation with system 100 is illustrated in flow chart form as procedure 200, which demonstrates a high level process flow diagram of some of the features provided by system 100. In one form, procedure 200 is at least partially implemented in the operating logic of system 100. Procedure 200 begins at start point 201 with selecting an image capture type (stage 202). In one embodiment, image capture type is selected using device selector 120.

If the image to be captured by image capture device 10 is an x-ray image (decision point 204), then a receptor holder (50 or 60) is attached to collimator tube 14 (stage 206). If the image is to be captured on x-ray film (decision point 208), then x-ray film is attached to receptor holder (50 or 60) (stage 210). If the image is to be captured using digital x-ray (decision point 208), then digital sensor 64 is attached to receptor holder 60 (stage 212). The x-ray generator 12 is then fired using firing switch 118 (stage 214) and the x-ray image(s) and/or video are captured (stage 216) by the film or the sensor 64.

If the image to be captured by image capture device 10 is not an x-ray image but instead is to be captured by digital camera (decision point 204), then digital camera 22 is fired using firing switch 118 (stage 218) and the digital image(s) and/or video are captured (stage 220).

If image(s) and/or video captured digitally with the x-ray generator 12 or the digital camera 22 are to be transmitted to a remote computer (decision point 222), then RF transmitter 20 sends the digital file(s) to RF receiver 114 of computer 102 (stage 224). If the image(s) and/or video captured digitally with the x-ray receptor 64 or the digital camera 22 are to be displayed in real-time (decision point 226), then frame grabber board 24 intercepts the images captured with sensor 64 or digital camera 22 accordingly and transmits them (using RF transmitter 20) to computer 102, video display device 104, or computer display 110 (stage 228). The process then ends at stage 230.

Referring now to FIGS. 16-20, an alternative collimator embodiment is illustrated incorporating a new alignment sensor to verify the alignment and orientation of the alignment ring on the square collimator tube in lieu of or in addition to contact sensor receptacle 28 described above. One prior production embodiment of contact sensor receptacle 28 utilized a Hall Effect sensor to detect the presence of magnets on the alignment ring. This included an indicator switch on the collimator tube to signal alignment of the alignment ring on the collimator tube. The Hall Effect sensor used included a degree of built in hysteresis. This permitted the alignment ring to come into alignment and activate the sensor. Then, if the alignment ring was moved out of alignment with the collimator by a small, but unacceptable, amount, the system would still indicate that alignment was correct when in fact it was unacceptably misaligned, resulting in cone cutting of the generated images due to the rectangular collimator tube.

FIGS. 16-20 illustrate a new alignment sensor and collimator that addresses some of the issues encountered with the prior sensor arrangement.

Figure 16:
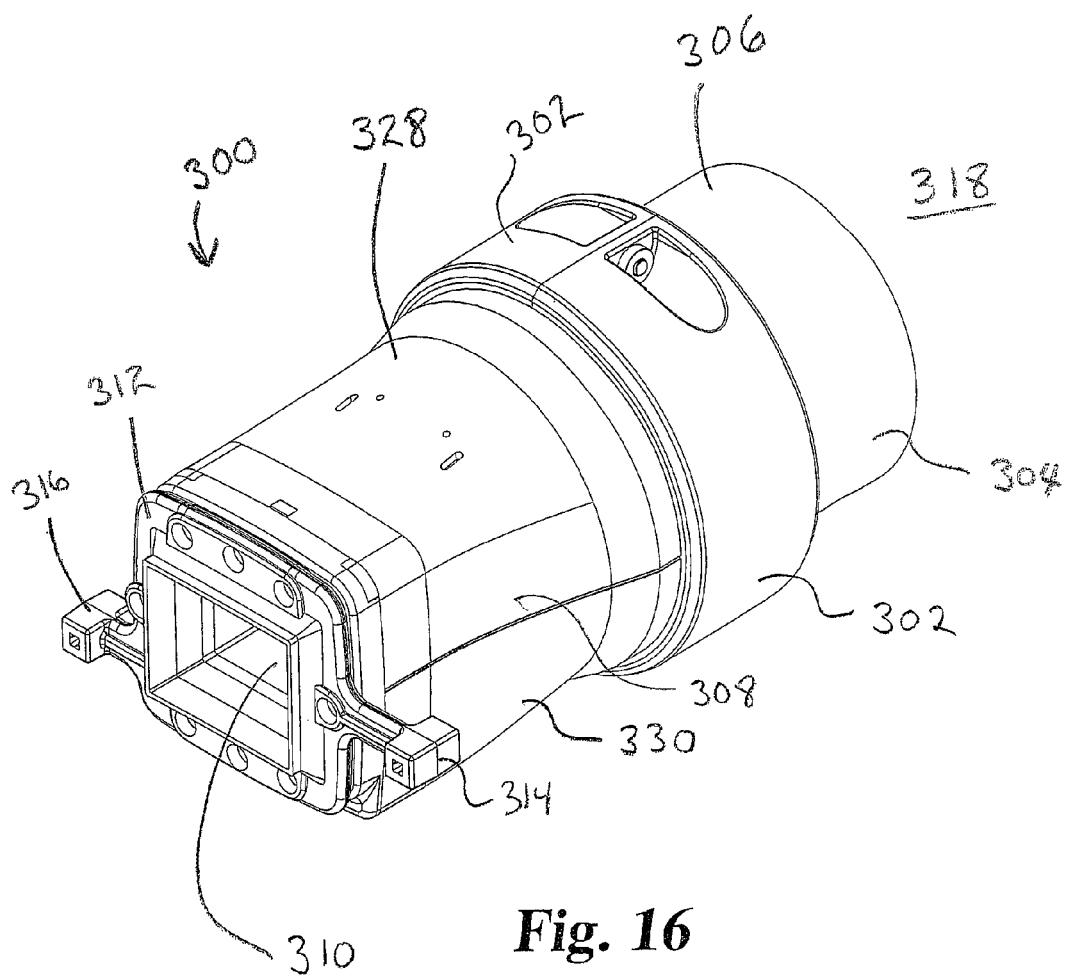
FIG. 16 is a perspective view of a rectangular collimator adapter coupled to a round collimator tube with a rectangular alignment ring attached to the rectangular collimator.

Referring to FIG. 16, adapter 300 is illustrated. Adapter 300 converts a prior art round profile collimator tube into a rectangular profile collimator tube with a reduced cross-section. The rectangular profile and reduced cross-section are configured to minimize the x-ray radiation emitted out of adapter 300 to match the area and shape of the film or sensor that captures the x-ray image.

Adapter 300 includes clamp 302 that affixes adapter 300 to round collimator tube 304 by clamping around outer periphery 306 of the end of round collimator tube 304 and housing 308 that surrounds rectangular collimator tube 310 and houses the sensor system described below. FIG. 16 also illustrates alignment ring 312 coupled to the end of housing 308 as described below.

Alignment ring 312 includes arms 314 and 316 that are configured to receive a receptor holder (not illustrated) that holds x-ray film or a digital sensor in alignment with rectangular collimator tube 310.

While not illustrated, round collimator tube 304 is operatively connected to x-ray source 318 that emits x-rays through round collimator tube 304.

Figure 17:
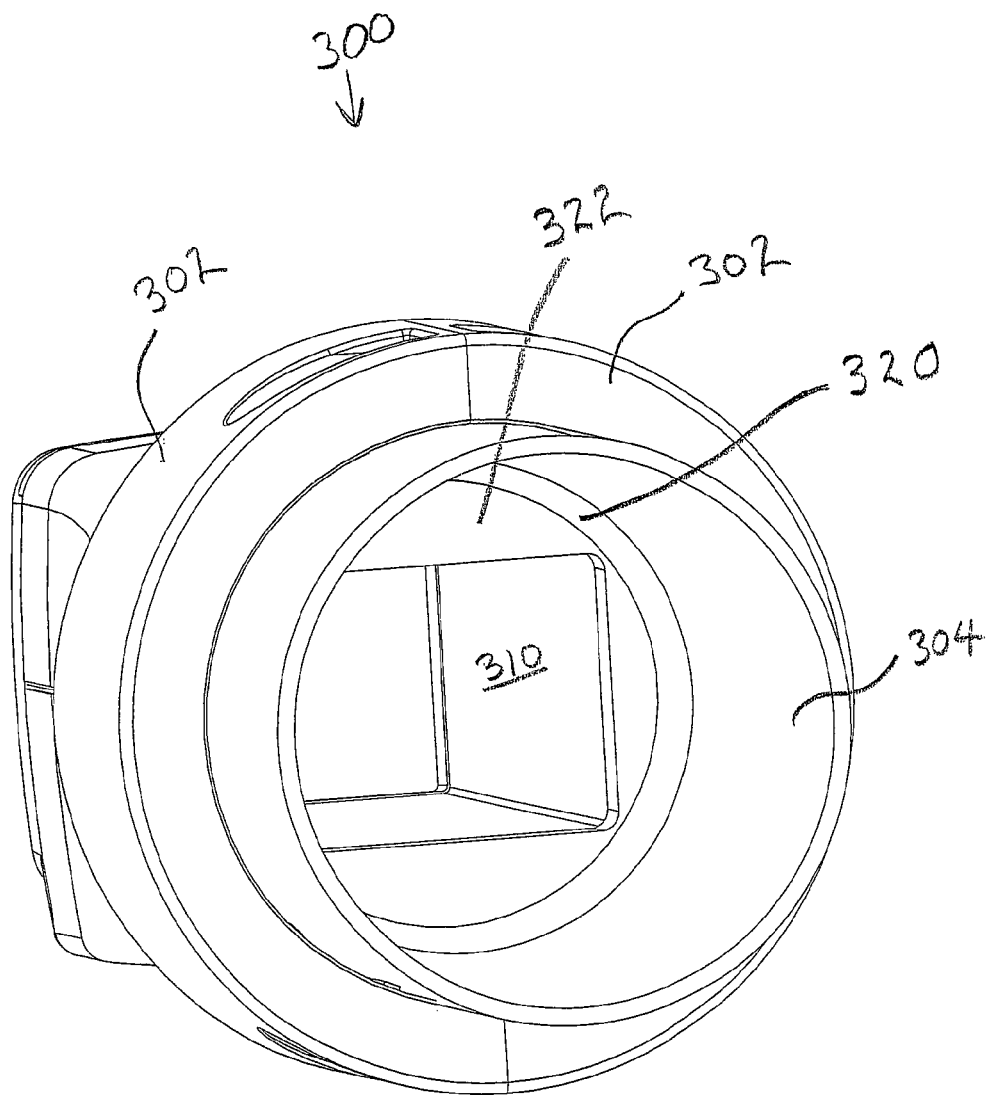
FIG. 17 is a rear perspective view of the FIG. 16 adapter.

Referring to FIG. 17, a portion of round collimator tube 304 is illustrated inserted into adapter ring 320. Adapter ring 320 includes plate 322 that transitions the shape of round collimator tube 304 to rectangular collimator tube 310. Plate 322 is held within adapter ring 320.

Figure 18:
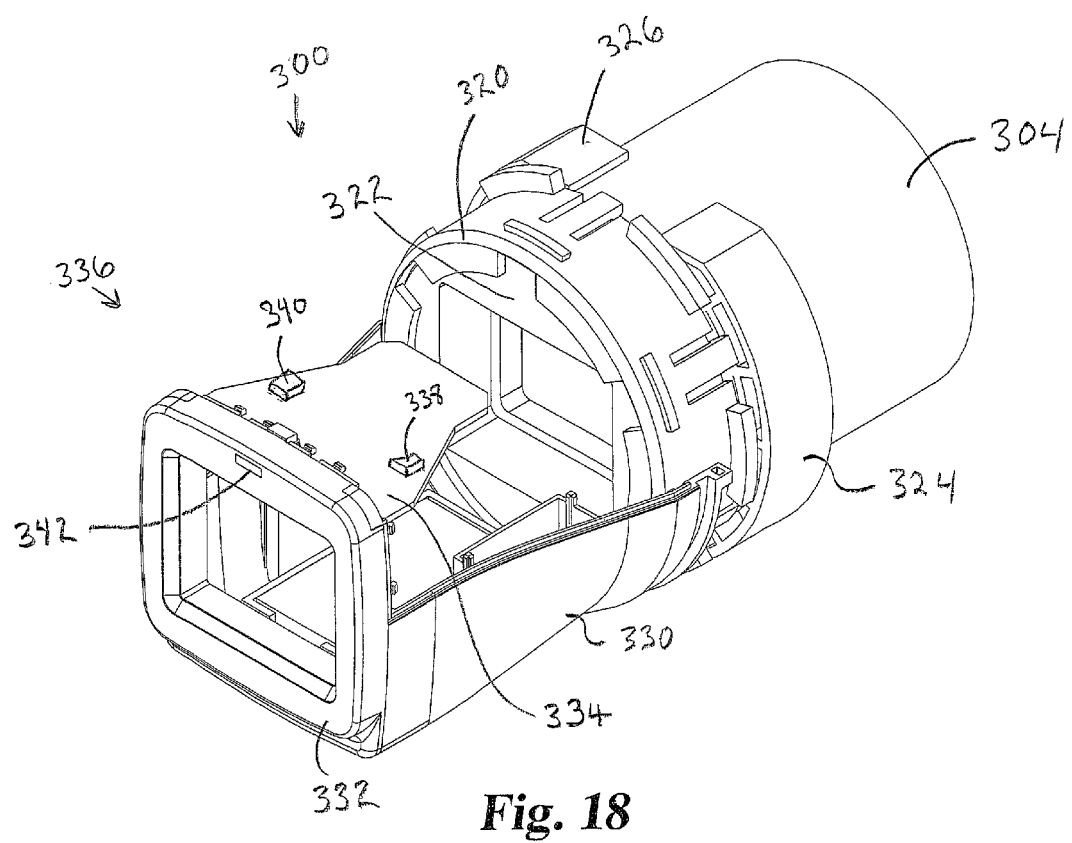
FIG. 18 is a cut away view of the FIG. 16 adapter.

Referring to FIG. 18, additional details of adapter 300 are illustrated including lock collars 324 and 326 that are positioned underneath clamp 302 which directly interface with round collimator tube 304. Clamp 302 (illustrated in FIGS. 16 and 17) interfaces with lock collars 324 and 326 and adapter ring 320 to join adaptor 300 to round collimator tube 304. Housing 308 includes top cover 328 (shown in FIG. 16) and bottom cover 330. Housing 308 also includes face plate 332 that is configured to receive alignment ring 312, as described below.

Support plate 334 between top cover 328 and rectangular collimator tube 310 supports sensor system 336. Sensor system 336 includes light source 338 and light detector 340. Light source 338 is oriented to shine an emitted coherent light beam at window 342 in face plate 332. The light detector is configured to intercept the coherent light beam when it is reflected off of a reflective surface positioned flush against window 342. This is described in more detail below.

Figure 19:
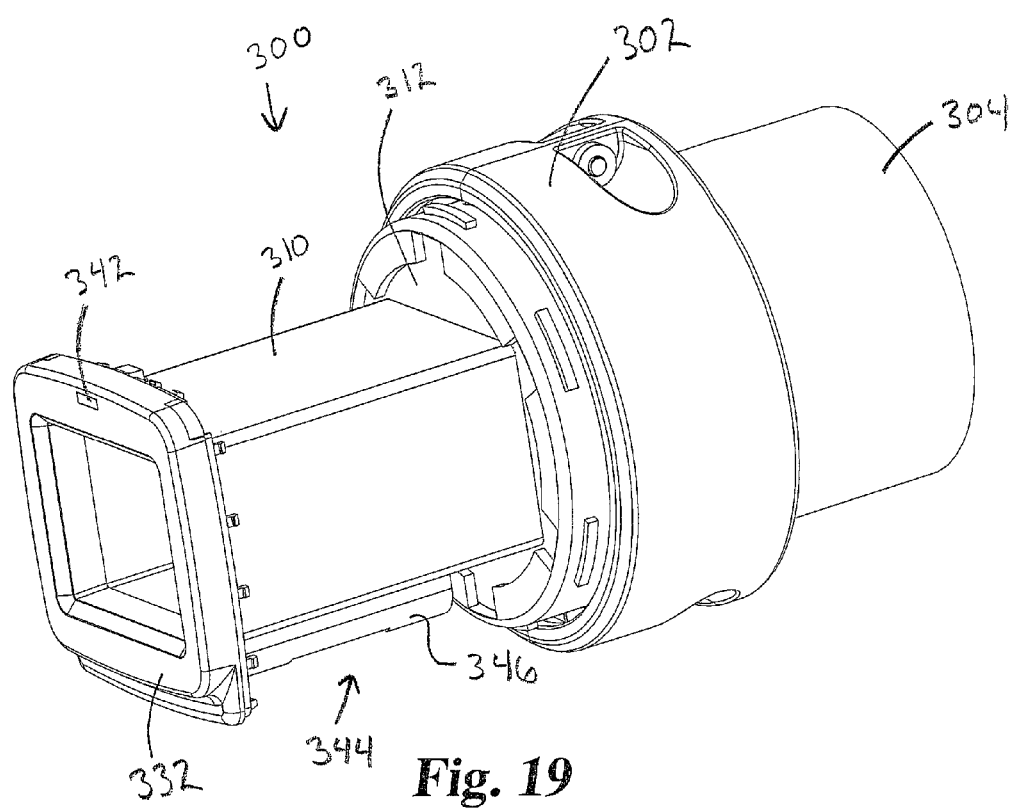
FIG. 19 is a side perspective cut away view of the FIG. 16 adapter.

Referring to FIG. 19, rectangular collimator tube 310 is illustrated without covers 328 and 330 showing alignment ring 312 affixing to round collimator tube 304 by clamp 302 with face plate 332 on the end of the rectangular collimator tube 310. Also illustrated in FIG. 19 is battery compartment 344 located underneath rectangular collimator tube 310 holding battery 346. Battery 346 powers sensor system 336 described below.

Figure 20:
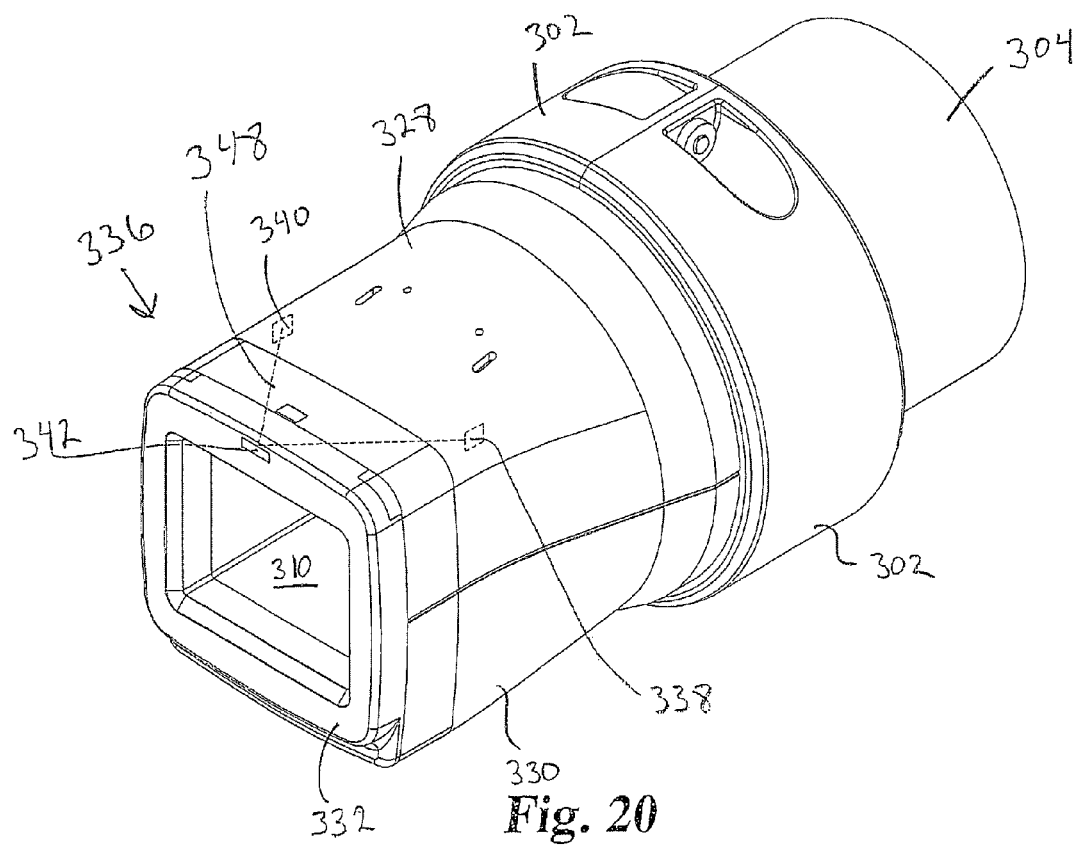
FIG. 20 is a perspective view of FIG. 16 adapter with the alignment ring removed.

Referring to FIG. 20, sensor system 336 is shown in adapter 300 with light source 338 and light detector 340 illustrated by hidden lines showing the intended light path 348 to and from the window between light source 338 and light detector 340 (when alignment ring 312 is correctly located in front of window 342 as described below).

Figure 21:
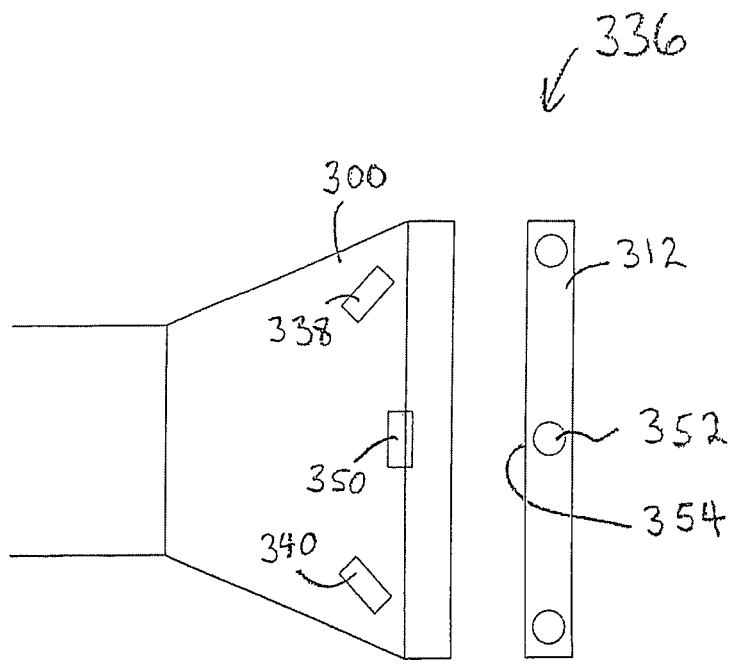
FIG. 21 is a schematic view of the disclosed alignment ring sensor system in a near proximity configuration.
Figure 22:
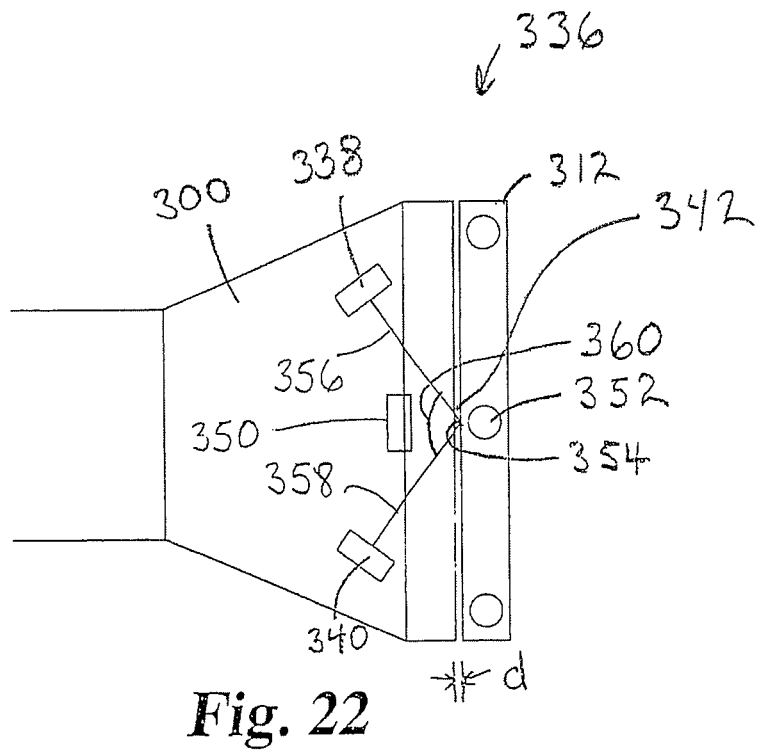
FIG. 22 is a schematic view of the disclosed alignment ring sensor system in close proximity and alignment.
Figure 23:
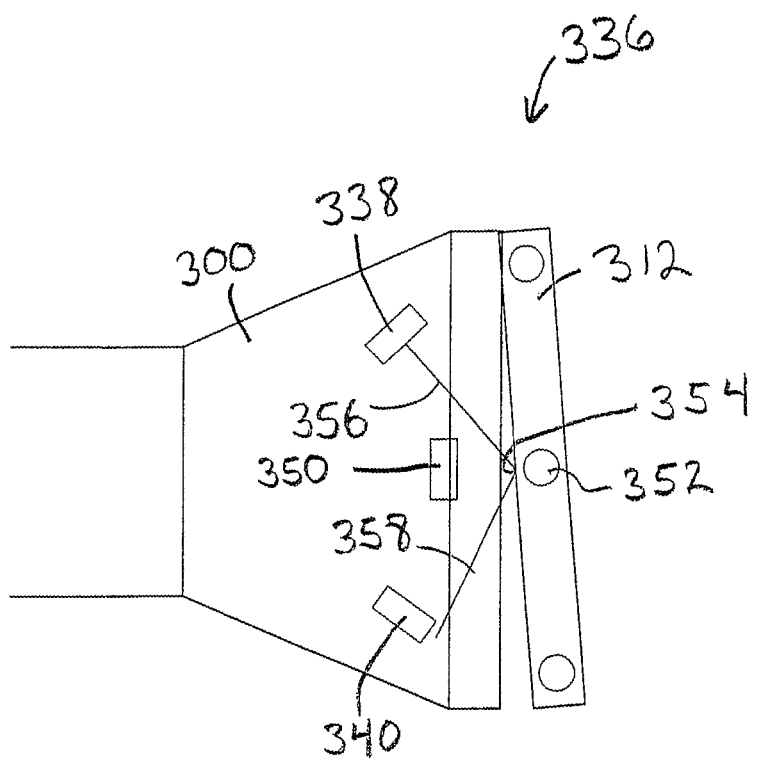
FIG. 23 is a schematic view of the disclosed alignment ring sensor system in close proximity and misaligned.

Referring to FIGS. 21-23, the operation of sensor system 336 is illustrated. As shown in FIG. 21, sensor system 336 includes magnetic sensor 350 operable to detect magnet 352 in alignment ring 312. FIG. 22 shows the described configuration of light source 338 and light detector 340 including reflective surface 354 positioned on alignment ring 312. In the illustrated embodiment, light source 338 is an IR LED Laser and light detector 340 is an IR detector. As illustrated in FIG. 22, light source 338 is arranged in adapter 300 so that the IR laser light 356 incident on reflective surface 354 reflects with resultant reflected laser light 358 diverging from incident IR laser 356 by reflection angle 360.

In the illustrated configuration, reflection angle 360 is obtuse and equal to approximately 100 degrees. In other configurations, sensor system 336 can be configured such that reflection angle 360 traverses between approximately 10 degrees and approximately 170 degrees. In various embodiments, reflection angle 360 is dependent upon the distance of light detector 340 from reflective surface 354 and the sensitivity of light detector 340. A larger reflection angle 360 provides more sensitivity to the distance of alignment ring 312 from adapter 300. A smaller reflection angle may provide more lateral space to locate light source 338 and light detector 340 and may allow light detector 340 to be located further away from reflective surface 354 which generally increases sensitivity to angular misalignments between alignment ring 312 and adapter 300.

In FIG. 22, alignment ring 312 is precisely aligned with adapter 300 resulting in IR laser light 356 being reflected as reflected laser light 358 at light detector 340. Or stated another way, reflective surface 354 on alignment ring 312 bisects reflection angle 360, in all planes, between light detector 340 and light source 338.

Referring to FIG. 23, a misaligned situation is illustrated where alignment ring 312 is not aligned with the face of adapter 300 so that reflected laser light 358 reflecting off reflective surface 354 on alignment ring 312 is not received by light detector 340.

In the embodiment illustrated in FIG. 21, sensor system 336 utilizes a combination of magnets with a Hall Effect magnet sensor 350 to provide a wake up signal to activate sensor system 336 from a power saving mode. Sensor 350 is not used for indicating alignment of adapter 300 and alignment ring 312. In order to detect or to verify proper alignment of alignment ring 312 and light source 338 emits IR laser beam 356 with a narrow beam which is projected out towards window 342 and is reflected off of reflective surface 354 on alignment ring 312. Only when reflective surface 354 on alignment ring 312 is in the correct position does IR laser beam 356 reflect at exactly the correct angle 360 to intersect light detector 340. Any misalignment in any of the three planes (vertical axis, horizontal axis or distance) will cause the laser beam to miss being reflected back to the IR detector.

Sensor system 336 can be used as an interlock switch to verify alignment of alignment ring 312 with adapter 300 (and rectangular collimator tube 310) before activating x-ray source 318. In this way, sensor system can reduce or eliminate poor x-ray images caused by cone cutting while minimizing the cross-sectional area of x-rays emitted out of rectangular collimator tube 310.

As shown in FIG. 21, magnetic sensor 350 may be configured to detect magnet 352 when alignment ring 312 is in close proximity. For example, within approximately one inch. FIG. 21 shows a close proximity situation between magnetic sensor 350 and alignment ring 312 (and magnet 352). Magnetic sensor 350 would activate the voltage from battery 346 and awaken the processor controlling sensor system 336.

Once the processor is awakened or powered up, it monitors light detector 340 to establish if the threshold of the ambient light (detected before emitting light from light source 338) is higher than a specific background light tolerance level. If it is, then a ready LED activates in a steady state indicating to the user that the background light level is too high and sensor system 336 will not able to reliably detect alignment in the current lighting condition.

Otherwise, under a normal condition, alignment is achieved when light source 338 emits pulsed light beam 356 out of a transparent cover on window 342 which bounces off reflective surface 354 on alignment ring 312 which reflects beam 358 back through window 342 to be detected by light detector 340. When properly aligned, as shown in FIG. 22, a green LED light may be illuminated and an audible beep may be provided. An additional beep may be provided if sensor system 336 detects misalignment (or lack of alignment) for more than one second. The green LED light on the collimator may remain lit as long as sensor system 336 detects alignment which indicates to the user a proper alignment at any particular instance. This real-time feedback can be observed by the operator to determine whether an x-ray should be taken at a particular instance.

If the alignment ring is out of alignment in any of the three planes (as shown in FIG. 23) then reflected laser light 358 is not reflected back to light detector 340 and the green LED light is not illuminated.

Alternatively, or in addition, sensor system 336 can act as a permissive interlock, only permitting an x-ray to be taken when light detector 340 actively detects light.

Two switches may also optionally be provided on top of adapter 300. One is to calibrate the sensor system 336 and the other is to mute the optional beep sound.

Figure 24:
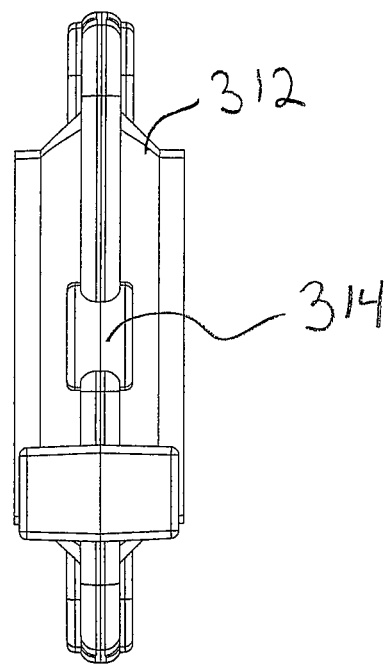
FIG. 24 is a side elevational view of a the FIG. 16 alignment ring.
Figure 25:
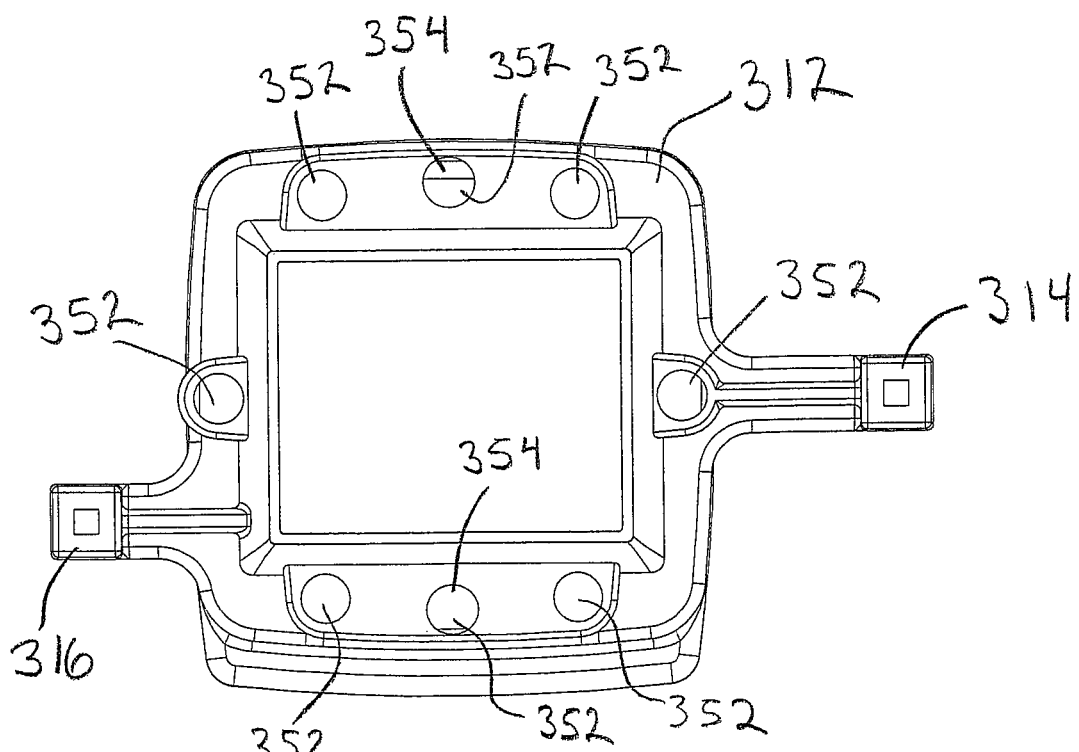
FIG. 25 is a front elevational view of the FIG. 24 alignment ring.

Referring to FIGS. 24 and 25, alignment ring 312 is illustrated including eight magnets 352 spaced around alignment ring 312. Magnets 352 interact with steel metal plates inside faceplate 332 on adaptor 300 to hold alignment ring 312 on adaptor 300, as shown in FIG. 16. Magnets 352 are sufficiently strong to hold alignment ring 312 and connect alignment ring 312 and a sensor or film (not illustrated) aligned with rectangular collimator tube 310 while still permitting alignment ring 312 to decouple from adapter 300 if the patient turns or otherwise moves their head.

The magnets 352 have a reflective surface 354 used in the above described sensor system 336. These surfaces of the various magnets to permit alignment ring 312 to be used in multiple orientations.

While sensor system 336 is only illustrated on adaptor 300, it should be understood that sensor system 336 could be incorporated in any collimator tube adaptor or directly in a OEM collimator tube This disclosure serves to illustrate and describe the claimed invention to aid in the interpretation of the claims. However, this disclosure is not restrictive in character because not every embodiment covered by the claims is necessarily illustrated and described. All changes and modifications that come within the scope of the claims are desired to be protected, not just those embodiments explicitly described.

We claim:

1. A system for aligning a collimator and an alignment ring, the system comprising:
    a light source;
    a light detector;
    a reflective surface, wherein the light source, the light detector and the reflective surface are constructed and arranged so that, when the collimator and alignment ring are aligned, light emitted from the light source reflects off the reflective surface and is received by the light detector; and
    a magnetic sensor and a magnet, wherein the magnetic sensor detects when the magnet is in close proximity and wherein the magnetic sensor is coupled to the light source and light detector and activates the light source and light detector when the magnetic sensor detects that the magnet is in close proximity.

2. The system of claim 1, wherein the light source emits a collimated beam of light.

3. The system of claim 1, wherein the light source emits a laser light beam.

4. The system of claim 1, wherein the light source and the light detector are affixed to the collimator and the reflective surface is affixed to the alignment ring.

5. The system of claim 1, wherein, when the collimator and alignment ring are aligned and light emitted from the light source reflects off the reflective surface and is received by the light detector, the reflection angle of the reflected light is between approximately 10 degrees and approximately 170 degrees.

6. The system of claim 1, wherein, when the collimator and alignment ring are aligned and light emitted from the light source reflects off the reflective surface and is received by the light detector, the reflection angle of the reflected light is an obtuse angle.

7. The system of claim 1, wherein, when the collimator and alignment ring are aligned and light emitted from the light source reflects off the reflective surface and is received by the light detector, the reflective surface bisects the reflection angle of the reflected light in all planes.

8. The system of claim 1, wherein the light source, the light detector and the reflective surface are constructed and arranged so that, when the collimator and alignment ring are misaligned, light emitted from the light source is not received by the light detector.

9. The system of claim 5, wherein the light source, the light detector and the reflective surface are constructed and arranged so that, when the collimator and alignment ring are misaligned, light emitted from the light source is not received by the light detector.

10. The system of claim 3, wherein the light source and the light detector are affixed to the collimator and the reflective surface is affixed to the alignment ring.

11. The system of claim 10, wherein, when the collimator and alignment ring are aligned and light emitted from the light source reflects off the reflective surface and is received by the light detector, the reflection angle of the reflected light is between approximately 10 degrees and approximately 170 degrees.

12. The system of claim 10, wherein, when the collimator and alignment ring are aligned and light emitted from the light source reflects off the reflective surface and is received by the light detector, the reflection angle of the reflected light is an obtuse angle.

13. The system of claim 10, wherein, when the collimator and alignment ring are aligned and light emitted from the light source reflects off the reflective surface and is received by the light detector, the reflective surface bisects the reflection angle of the reflected light in all planes.

14. The system of claim 10, wherein the light source, the light detector and the reflective surface are constructed and arranged so that, when the collimator and alignment ring are misaligned, light emitted from the light source is not received by the light detector.

15. The system of claim 12, wherein the light source, the light detector and the reflective surface are constructed and arranged so that, when the collimator and alignment ring are misaligned, light emitted from the light source is not received by the light detector.

* * * * *